United States Patent
Wieczorek et al.

(10) Patent No.: US 10,031,098 B2
(45) Date of Patent: Jul. 24, 2018

(54) MULTI-CONDUCTOR WATER IN FUEL SENSOR FOR FILL RATE DETECTION

(71) Applicant: CUMMINS FILTRATION IP, INC., Columbus, IN (US)

(72) Inventors: Mark T. Wieczorek, Cookeville, TN (US); Dean H. Dringenburg, Seymour, IN (US); Rahul B. Kallurwar, Columbus, IN (US)

(73) Assignee: CUMMINS FILTRATION IP, INC., Columbus, IN (US)

(*) Notice: Subject to any disclaimer, the term of this patent is extended or adjusted under 35 U.S.C. 154(b) by 22 days.

(21) Appl. No.: 15/231,198

(22) Filed: Aug. 8, 2016

(65) Prior Publication Data

US 2016/0349200 A1 Dec. 1, 2016

Related U.S. Application Data (62) Division of application No. 13/092,310, filed on Apr. 22, 2011, now Pat. No. 9,453,754.

(60) Provisional application No. 61/328,391, filed on Apr. 27, 2010.

(51) Int. Cl.
   G01N 27/06 (2006.01)
   B01D 36/00 (2006.01)
   G01F 23/24 (2006.01)
   G01N 33/28 (2006.01)

(52) U.S. Cl.
   CPC ......... *G01N 27/06* (2013.01); *B01D 36/005* (2013.01); *G01F 23/242* (2013.01); *G01N 33/2847* (2013.01)

(58) Field of Classification Search
   CPC .................................................. B01D 36/005
   See application file for complete search history.

(56) References Cited

U.S. PATENT DOCUMENTS

| | | |
|---|---|---|
| 3,986,110 A | 10/1976 | Overall et al. |
| 5,083,459 A | 1/1992 | Lind et al. |
| 2005/0229699 A1 | 10/2005 | Chai et al. |

(Continued)

FOREIGN PATENT DOCUMENTS

| | | |
|---|---|---|
| JP | 07-114416 | 5/1995 |
| JP | 11-311562 | 11/1999 |
| KR | 102003002533 | 3/2003 |

OTHER PUBLICATIONS

International Search Report for International Application No. PCT/US2011/033569, dated Jan. 2, 2012 (3 pages).

(Continued)

*Primary Examiner* — Peter Keyworth
(74) *Attorney, Agent, or Firm* — Foley & Lardner LLP (57) ABSTRACT

A water sensor for a fuel filtration apparatus includes a main body with at least one electrical contact disposed proximate the first end of the main body. The electrical contact(s) is operatively connectable to an electronic control unit. Multiple sensor contacts are disposed proximate a second end of the main body. The sensor contacts are configured to detect multiple water levels and provide an output on each water level detected. The electrical contact is configured to send the output to an electronic control unit. The water level information provided by the water sensor can be tracked by a control device to determine if the fill rate of water meets an alarm value.

20 Claims, 9 Drawing Sheets

Condition Table

| Water Level | Resistance across pins A/B |
|---|---|
| 1 | 100 kΩ |
| 2 | >150 kΩ |
| 3 | Lowest value |

(56) References Cited

U.S. PATENT DOCUMENTS

2007/0079653 A1    4/2007  Zuleta et al.
2009/0103904 A1    4/2009  Wolff et al.
2009/0278699 A1*  11/2009  Horst ...................... G01F 23/24
                                                      340/603

OTHER PUBLICATIONS

Written Opinion of the International Search Authority for International Application No. PCT/US2011/033569, dated Jan. 2, 2012 (6 pages).

* cited by examiner

Condition Table

| Water Level | Resistance across pins A/B |
|---|---|
| 1 | 100 kΩ |
| 2 | >150 kΩ |
| 3 | Lowest value |

Fig. 4

Condition Table

| Water Level | Resistance across pins A/B |
|---|---|
| 1 | 200 kΩ |
| 2 | < 200 kΩ |
| 3 | < 50 kΩ |

Fig. 5

$t_{REF}$
* Stored to memory

MULTI-CONDUCTOR WATER IN FUEL SENSOR FOR FILL RATE DETECTION

This application is a divisional of U.S. patent application Ser. No. 13/092,310, filed Apr. 22, 2011, which claims the benefit of U.S. Provisional Application Ser. No. 61/328,391, filed on Apr. 27, 2010, and titled "Multi-Conductor Water in Fuel Sensor for Fill Rate Detection." The contents of both applications are hereby incorporated by reference in their entirety.

FIELD

This disclosure pertains to detecting water content. Particularly, a water in fuel sensor is described, for example, within a diesel fuel filtration apparatus, that detects when a high content of water has entered a collection area of the filtration apparatus. The water in fuel sensor entails the use of multiple contacts allowing detection of multiple different water levels. The water in fuel sensor provides water level information that can be tracked by a suitable control device, for example an engine control unit, to determine if the fill rate of water meets an alarm value.

BACKGROUND

The vast majority of available fuel filtration systems incorporate an electrical sensor, often known as a water in fuel (WIF) sensor, to detect a certain volume of water accumulated in the collection area of a filter module, such as its sump. While current technology can detect the level of water accumulated in the sump, regardless of the time in which it was accumulated, improvements can be made to such water in fuel sensors.

SUMMARY

A means is described to limit the occurrence of water related corrosion or damage to various engine components by detecting when a high content of water has entered a collection area, so that a vehicle operator may be notified before damage is caused. Generally, a water in fuel sensor is described that detects when a high content of water has entered a collection area of the filtration apparatus. The water in fuel sensor in many cases is employed in a diesel fuel filtration apparatus, such as in a sump of a fuel water separator apparatus, but may be employed in other applications where appropriate. The water in fuel sensor has multiple contacts allowing detection of multiple different water levels. The water in fuel sensor provides water level information that can be tracked by a suitable control device, for example an engine's electronic control unit, which may employ a software routine if appropriate, to determine if the fill rate of water meets an alarm value.

In one embodiment, a water sensor described herein is for a fuel filtration apparatus. The water sensor includes a main body having a first end and a second end. At least one electrical contact is disposed proximate the first end and operatively connectable to an electronic control unit. Multiple sensor contacts are disposed proximate the second end. The sensor contacts are configured to detect multiple water levels and provide an output on each water level detected. The at least one electrical contact is configured to send the output to an electronic control unit.

In certain circumstances, two electrical contacts may be used. In other embodiments, where appropriate, a single contact may also be employed, for example, if the water sump is conductive and in electrical contact with a body of the vehicle, such that the "ground" circuit passes through the vehicle's body, so that this path completes the electrical circuit to the control unit. Such a configuration may be designed for example, in advance by an engine manufacture, and could result in a lower cost application, by elimination of one circuit and its associated wire, connector, and pins.

The electronic control unit may be any suitable control device for interpreting the sensor inputs as described, including, but not limited to, an Engine Control Module (ECM), a controller, fluid management control module, or any suitable data/information processing device, and which may employ a software routine.

Various sensor technologies can be incorporated into the fuel filtration module to determine water content accumulated in the fuel filtration module sump.

DETAILED DESCRIPTION

Generally, a water in fuel sensor as described herein has multiple contacts allowing detection of multiple different water levels. The water in fuel sensor in many cases is employed in a diesel fuel filtration apparatus, such as in a sump of a fuel water separator apparatus, but may be employed in other applications where appropriate. The contacts of the water in fuel sensor provide water level information that can be tracked by a suitable control device, for example an engine control unit, to determine if the fill rate of water meets an alarm value. The water in fuel sensor can help to limit the occurrence of water related corrosion or damage to various engine components, so that a vehicle operator may be notified before damage is caused.

More generally, the sensor described herein provides multi-level resistance sensing, particularly a resistance based level switch sensor that can detect a rate of change of water accumulation in a filtration module sump or the fuel tank sump. The sensor is configured to have different water accumulation detection levels and change output signals at each level. The time interval between triggering of detection levels is compared against a pre-defined time interval, and if the detected time interval is greater than the pre-defined time interval, high water content fuel has been detected.

As one example, a water in fuel sensor has a multiconductor configuration employing the use of three or more electrical conductors. Generally, the water in fuel sensor is meant to be oriented in a water collection area (e.g. sump) of a diesel fuel water separator, such that the conductors are sequentially submerged by water as water is collected.

Figure 1A:
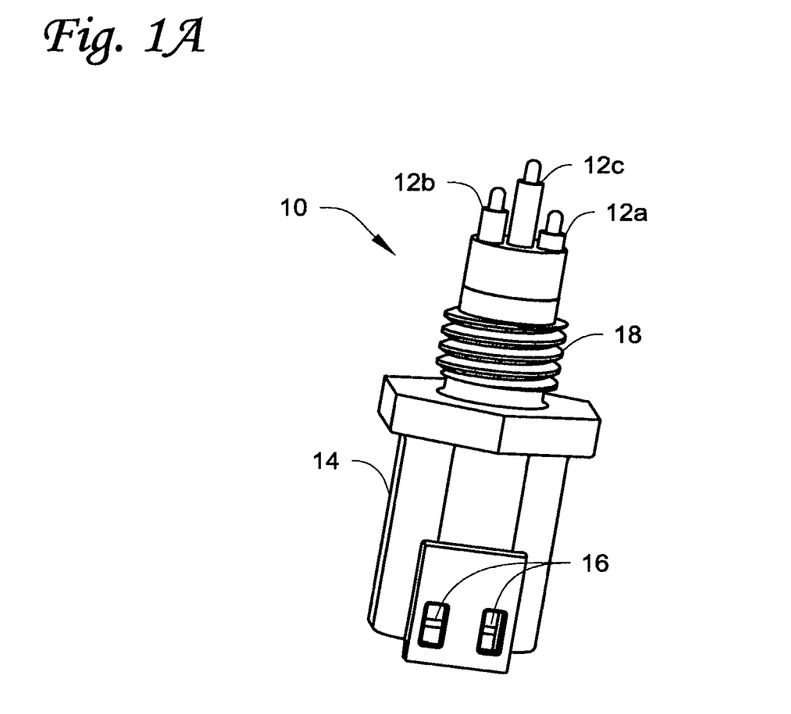
FIG. 1A shows one embodiment of a multiconductor water in fuel sensor having three conductors of different lengths.

FIG. 1A shows a water sensor 10 that includes a main body having a first end and a second end. At least one electrical contact 16 is disposed proximate the first end and operatively connectable to an electronic control unit (not shown). Multiple sensor contacts 12a, 12b, 12c are disposed proximate the second end. Each sensor contact 12a, 12b, 12c of the multiple sensor contacts can be configured to detect a different water level.

In some embodiments, where each of the sensor contacts 12a, 12b, 12c are in a water sump, the water sump is conductive at or below the height of the lowest pin (e.g. contact 12a) and is connected to a ground path of the electronic control unit, so that all three pins are able to detect separate water levels.

As shown in FIG. 1A, only two water levels are to be detected, where the lowest pin 12a is a ground pin. Both 12a and 12b must be submerged in water to detect the first water level, and 12a and 12c must be submerged to detect the second water level. The at least one electrical contact 16 is configured to send the different water level information obtained by each sensor contact to an electronic control unit. It will be appreciated that electronic control units, such as used in engines are well known and can be suitably configured to perform the processing and control needed to determine water level content and fill rate and are not further described.

With further reference to FIG. 1A, the three sensor contacts 12a, 12b, 12c or conductors are configured at different lengths extending from the main body 14, such that water sensor 10 can be installed vertically through a bottom of a water sump 202 of a water fuel separator 200 to detect different fill levels (see e.g. FIG. 8B further described below). As shown, the sensor contacts 12a, 12b, 12c are configured as pin-like structures.

Fuel has a very low conductivity, and for all practical purposes, can be considered an electrical insulator. Water, on the other hand, is relatively conductive due to the impurities in the water. As such, when no water is present, an open circuit will be seen by an engine's electronic control unit (ECU) across all pins relative to the shortest pin 12a, which serves as a reference point.

As the water level increases, both the shortest 12a and middle length 12b pins are submerged and resistance across these pins becomes low due to the high conductivity of water, while resistance between the shortest 12a and longest pins 12c remains high. As the water level continues to increase, all three pins 12a, 12b, 12c become submerged and resistance is low across all pairs of pins. In this way, the ECU (not shown) can detect the level of the water, and determine the water filling rate by comparing the time between reaching the first and second water levels. A high rate of water fill is indicative of a high water content of water in the fuel tank, which might require corrective action.

A thread 18 allows the water sensor 10 to connect to a water collection area (e.g. sump).

Figure 1B:
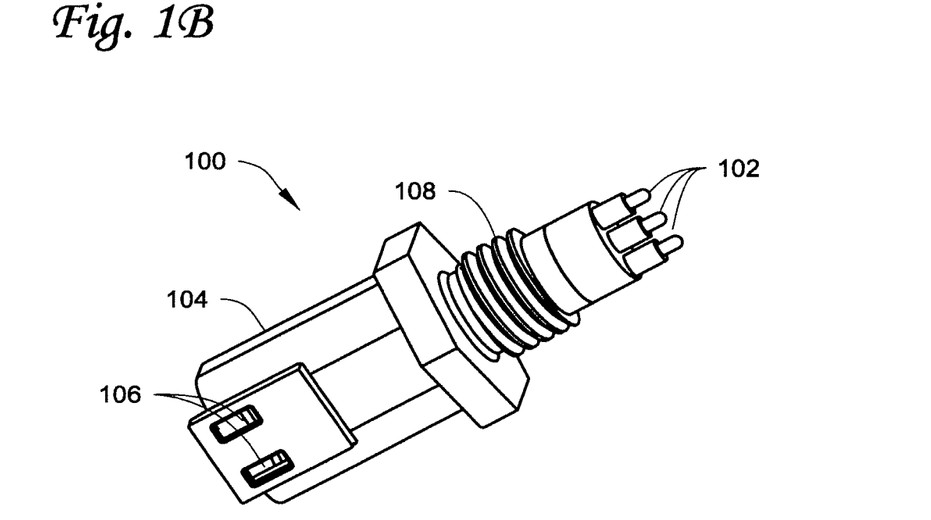
FIG. 1B shows another embodiment of a multiconductor water in fuel sensor having three conductors of equal lengths.

FIG. 1B shows a sensor 100 similarly constructed as the sensor 10 having a main body 104 and electrical contacts 106, but with three conductors 102 positioned for horizontal installation in the sump. The three conductors 102 are also pin-like structures of substantially the same length.

Figure 1C:
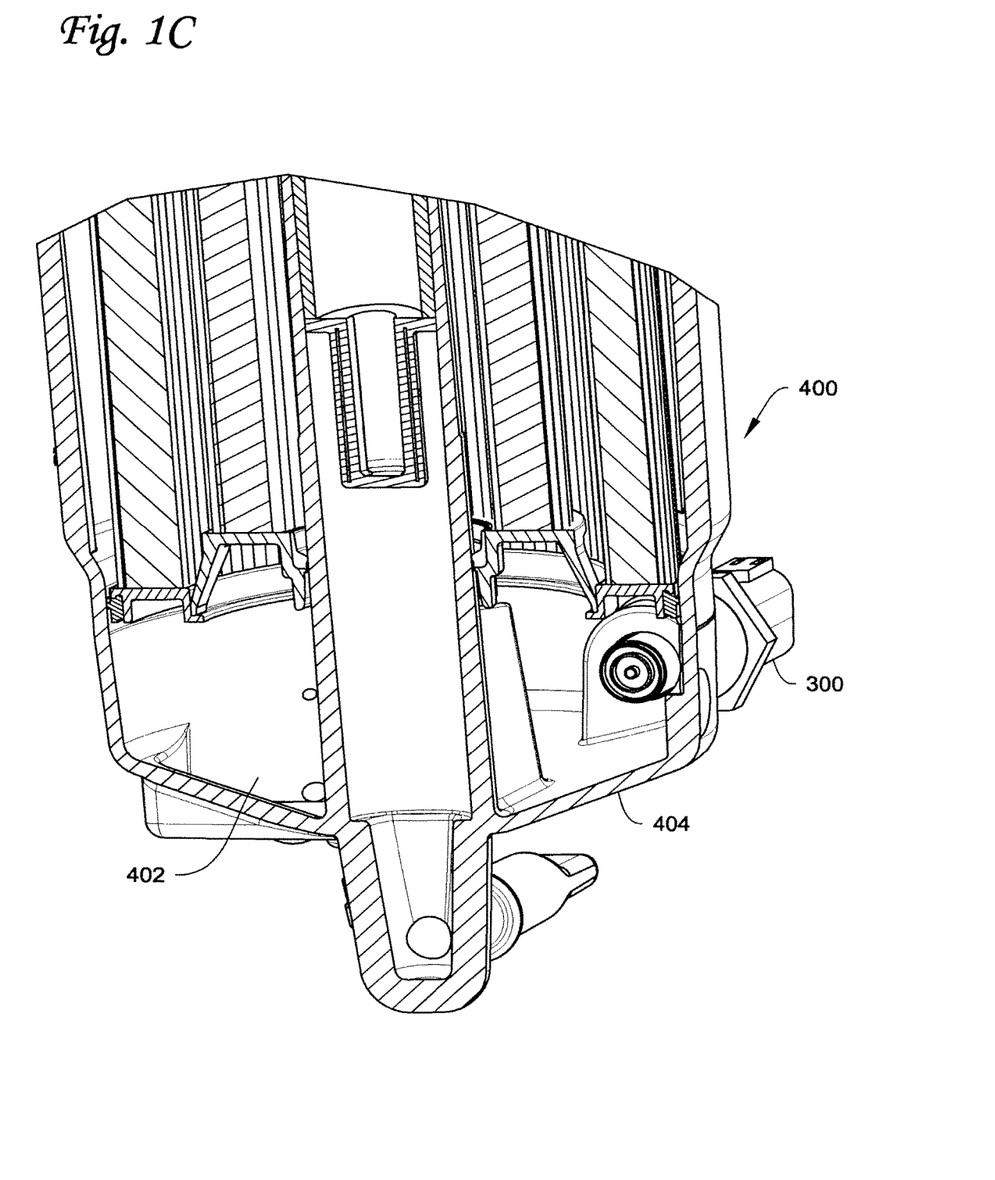
FIG. 1C shows an embodiment of a horizontal installation for another embodiment of a multiconductor water in fuel sensor having ring configured sensors, the horizontal installation shown is at a bottom of a fuel water separator housing such as for a fuel filter.

FIG. 1C illustrates an embodiment of horizontal installation of a water sensor in a bottom of a fuel water separator (FWS) housing. As shown, water sensor 300 having ring configured sensor contacts is shown horizontally installed in a bottom collection area, such as for example a sump 402 of a fuel water separator housing 404 that has a fuel filter 400. It will be appreciated that the sensor 100 of FIG. 1B may also be horizontally mounted in a similar manner as sensor 300.

With further reference to FIG. 1B, the three horizontal pins 102 in one embodiment can be oriented within a water sump of a fuel filtration apparatus, such that each pin 102 is approximately directly above the one below it. Such a configuration can provide a greater vertical distance between the pins, relative to the water level in the sump, allowing the sensor 100 to detect differences in water volume contained within the sump. To accomplish this orientation, the threads on the sensor and the mating water sump could be "clocked" or oriented such that the thread 108 always starts in nearly the same position for every product manufactured.

In the case of plastic parts, the sensor 100 could be welded into the housing by one of many methods, such as ultrasonic, spinwelding, vibration welding, or induction welding. Welding would also avoid the need for a seal between the two parts.

Another option is to not employ the thread 108, and instead use a flange (not shown) on the sensor, retaining it to the sump housing by a single or multiple screws. This method has the added benefit of removing the threads which take up considerable space, and limit the distance available to spread apart the sensor contact pins.

Figure 2:
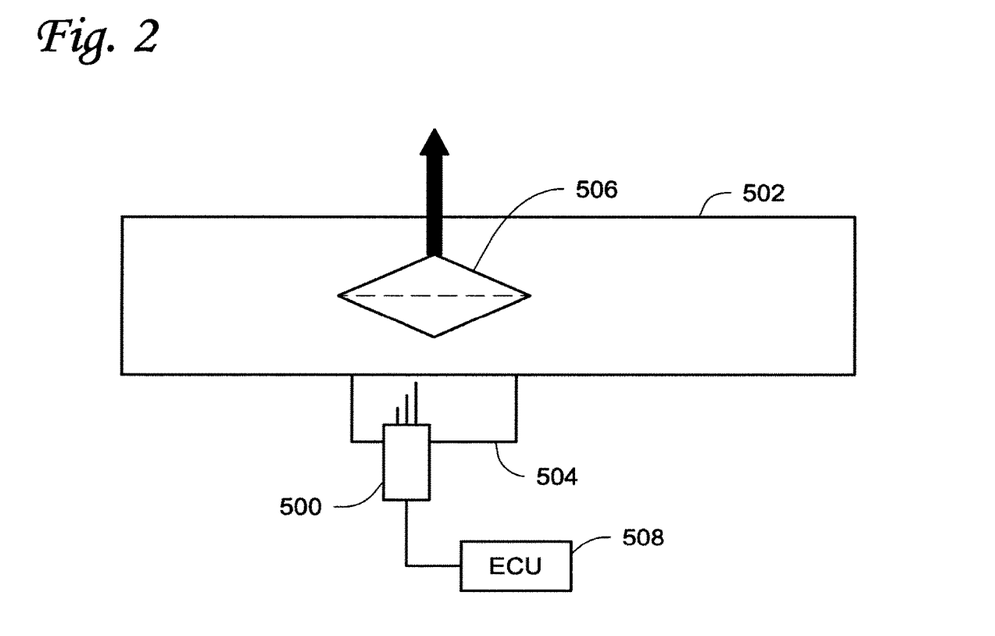
FIG. 2 shows a schematic of a multiconductor water in fuel sensor installed in a vehicle's fuel tank.

In other embodiments, a water sensor herein can be disposed in a vehicle's fuel tank. As shown in FIG. 2, for example, a sensor 500 could be located in the bottom of a vehicle's fuel tank 502 at a collection area 504. In some instances, a recess is formed in the bottom of the fuel tank 502 such that the water, which is more dense than fuel, settles there and can be readily detected by the sensor 500. As also shown in FIG. 2, an alternative is to include a fuel water separator 506 in the tank 502, to separate emulsified water from the fuel, allowing the sensor 500 to detect the water. The sensor 500 can send the information detected to an ECU 508. It will be appreciated that the ECU as employed herein, including ECU 508, may be any suitable control device for interpreting information detected by the sensor and may be but is not limited to, an known Engine Control Module (ECM), a controller, fluid management control module, or any suitable data/information processing device, and which may employ a software routine as appropriate. It will be appreciated that ECU 508 may be suitably employed with any of the sensors described herein.

Figure 3:
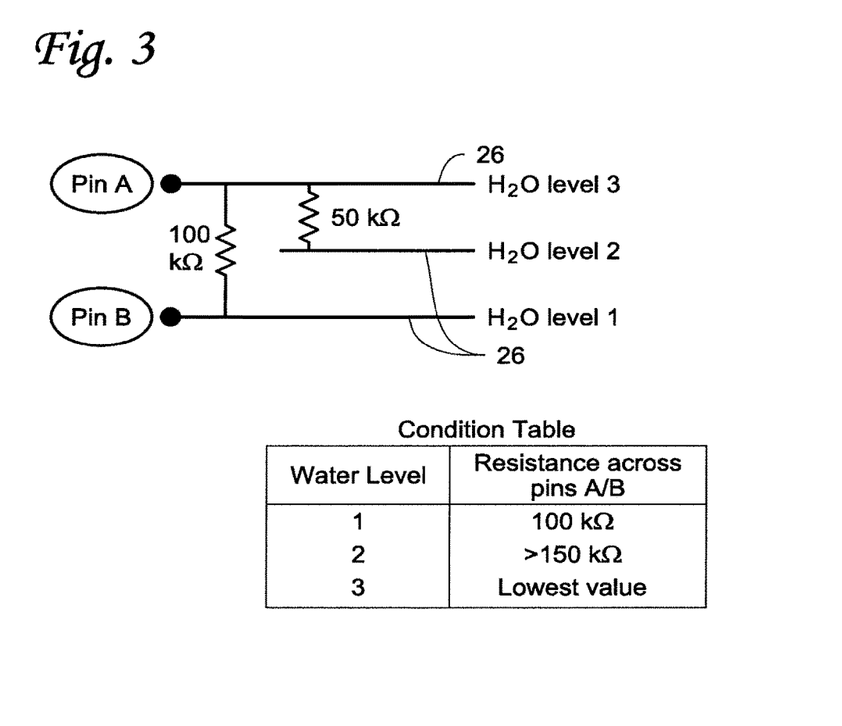
FIG. 3 shows the multiconductor water in fuel sensor of FIG. 1B having internal resistors, allowing for two-pin electrical connection to an engine control unit via electrical contacts or pins A and B.
Figure 4:
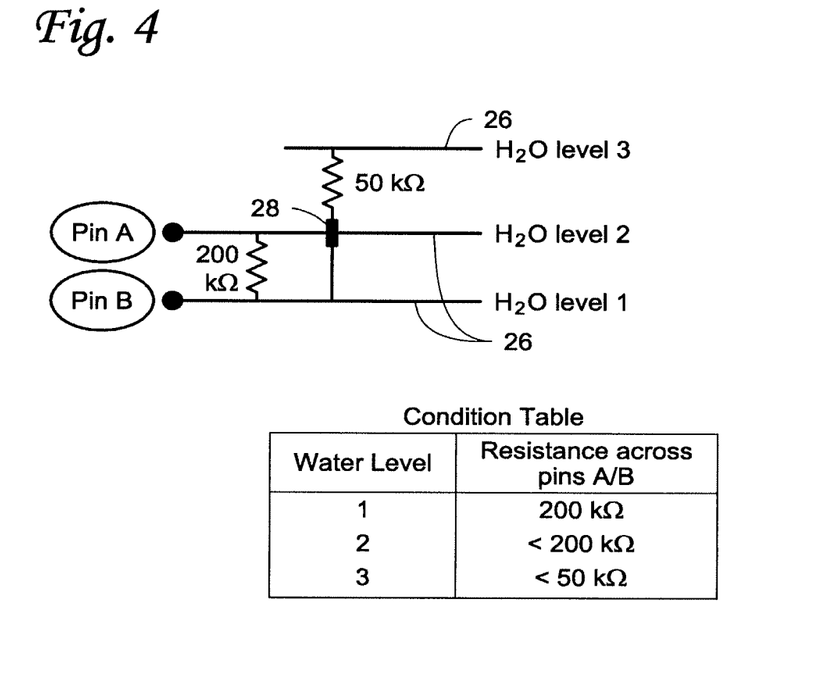
FIG. 4 shows an alternative resistor pattern and resulting condition table for electrical contacts or pins A and B.

With reference to the electrical connection between the sensors herein and an ECU, FIGS. 3 and 4 show alternative resistor patterns & resulting condition tables, respectively, where an ECU can connect to the water sensor via electrical contacts (e.g. electrical contacts 16) or pins A and B as shown in FIGS. 3 and 4. The resistor values shown are examples only. Different resistor values may be chosen as is convenient for the control unit designer. In a basic application of the sensors herein, three wires are used to go to the ECU, i.e. one for each sensor contact or pin, thereby using three electrical contacts. Another option, such as shown in FIGS. 3 and 4, requires only two electrical contacts or pin connections to the ECU. As shown, three wires 26 are used for each sensor contact and within the sensor, e.g. the main body, the use of resistors and insulators (e.g. 28) are incorporated as appropriate, so that the ECU can determine the water level with only a two-pin electrical contact connector. In such a configuration, the ECU measures the resistance across two electrical contacts (e.g. pins A and B), and can compare the measurements to values in a condition table, to determine the water level. See exemplary Condition Tables in FIGS. 3 and 4. It will be appreciated that the electrical contact configurations described above and shown in FIGS. 3 and 4 may be suitable employed in any of the water in fuel sensors described herein.

While two electrical contacts are used such as shown in FIGS. 3 and 4, other embodiments may be employed where appropriate. In certain circumstances, for example, when all three sensor contacts are to detect a water level, the water sensor may employ a single electrical contact, for example, if the water sump is conductive and in electrical contact with a body of the vehicle, such that the "ground" circuit passes through the vehicle's body, so that this path completes the electrical circuit to the control unit. Such a configuration may be designed for example, in advance by an engine manufacture, and could result in a lower cost application, by elimination of one circuit and its associated wire, connector, and pins.

Figure 5:
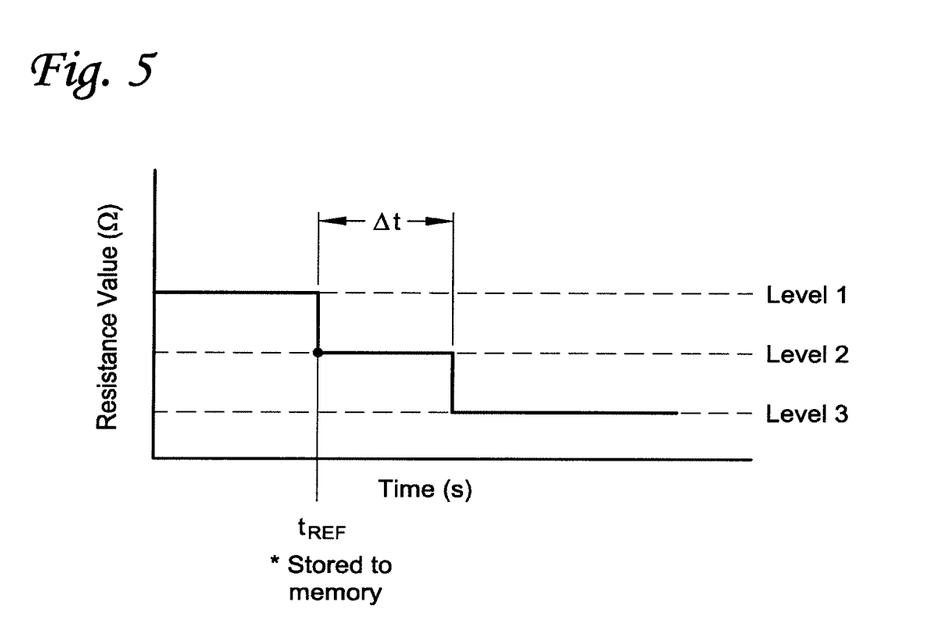
FIG. 5 shows an example of resistance that may be seen at the engine control unit over time as water fills a collection area or sump.

With reference to FIG. 5, resistance can be seen at the ECU over time as a water sump fills and the sensor contacts become submerged. FIG. 5 shows resistance for a water sensor having a resistor configuration similar to FIG. 4.

With reference to FIGS. 3-5, water level 1 is any condition where the water level is below the middle pin. Water level 2 is reached when the water level covers both the lowest and middle pins, and water level 3 is when the water contacts all three pins. As indicated by FIG. 5, for example, an ECU records the time at which level 2 is reached ($t_{REF}$) and then calculates $\Delta t$ when level 3 is reached. If $\Delta t$ is less than a predetermined value, then the ECU notifies an operator, such as the operator of the vehicle, via any suitable indicator such as light, sound, display, and the like, so that the operator can take appropriate action. Such action might include, for example: contacting an attendant at a fuel station that may have just sold the operator fuel with a high water content; treating the fuel in the tank with a corrosion preventative and anti-microbial treatment; changing the fuel filter: or having a service center drain and clean their fuel tank. Other actions may be appropriate depending on severity and cause of the high water content.

Figure 6:
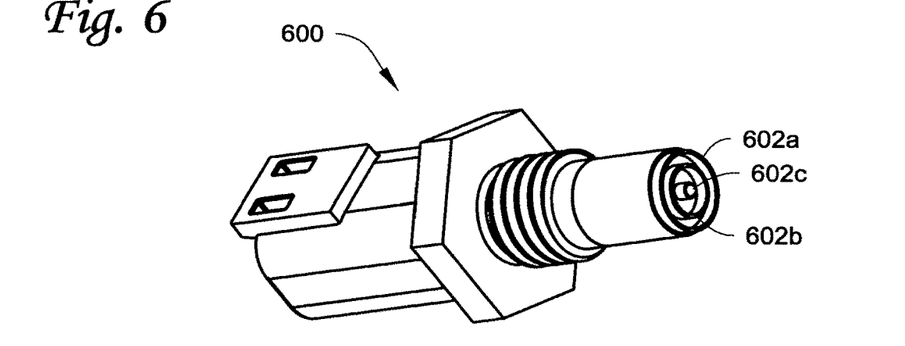
FIG. 6 shows another embodiment of a multiconductor water in fuel sensor with ring configured sensors.

With reference to FIG. 6, a water sensor 600 is shown as having sensor contacts 602a, 602b, and 602c, some of which may be configured as rings. Such a configuration does not require a certain rotational orientation when installing the water sensor 600.

The ring configuration of the sensor contacts provides an alternative design, for example, for horizontal installation within a sump. As shown, two conductive rings 602a, 602b and a center pin 602c make up the three electrical contacts within the water sump. In a horizontal installation configuration, the outer ring 602a would contact water first as the water level rose within the sump, followed by the inner ring 602b and finally the center pin 602c. No matter the rotational orientation, the distance between the three conductors would be about the same relative to the water in the sump.

It will be appreciated that the distance between the contacts 602a, 602b, and 602c can vary as appropriate or desired. To vary the distance between the contacts rings, the diameter of the rings may be increased or decreased.

One example to accomplish such a modification is to modify the end of the main body of the sensor. As one example, the threads on the outside of the sensor can be replaced with a flange or weld retention method, as discussed for the design shown in FIG. 1B, Contact rings of larger diameter could then be disposed on the flange.

Figure 7:
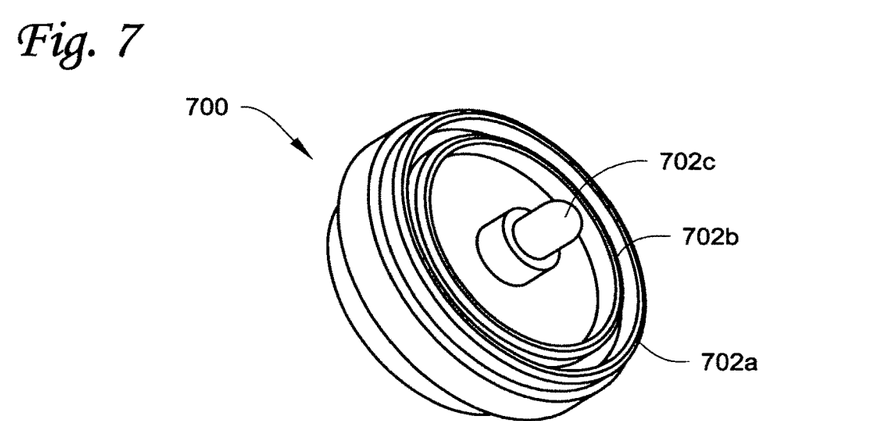
FIG. 7 shows an embodiment a multiconductor water in fuel sensor with a separable disc with the sensor contacts that can be attached/detached from a main body of the multiconductor water in fuel sensor after installation.

To achieve even greater diameter, a separate contact disc 700 can be attached to the sensor body after the body is installed in the water sump, such as illustrated in FIG. 7. This offers the ability to increase the contact ring diameter, such that it can be made larger than the clearance allowed by an installation hole provided by the water sump wall. Greater distance between the rings and pin, e.g. 702a, 702b, 702c, can allow more water to collect in the sump between level detections. The separate contact disc 700 in some embodiments may snap to the main body of the water sensor. Such disc 700 can allow flexibility of the diameter of the contact rings, and thus the amount of vertical water level rise between detection levels.

With reference to vertically oriented water sensors, FIGS. 8A-11B show additional embodiments of water sensors which may be useful for vertical installation, such as through the bottom of a water sump.

Figure 8A:
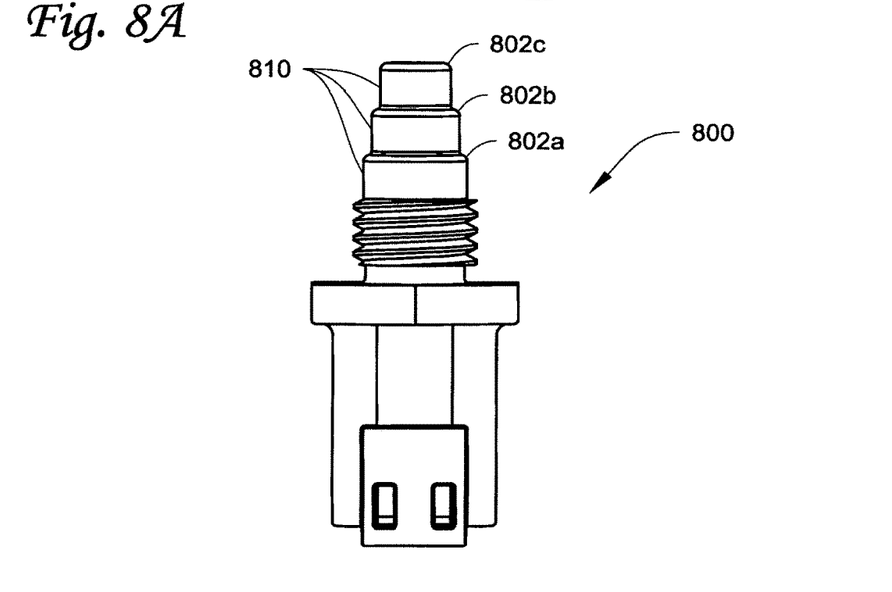
FIG. 8A shows an embodiment of a vertically oriented multiconductor water in fuel sensor.
Figure 8B:
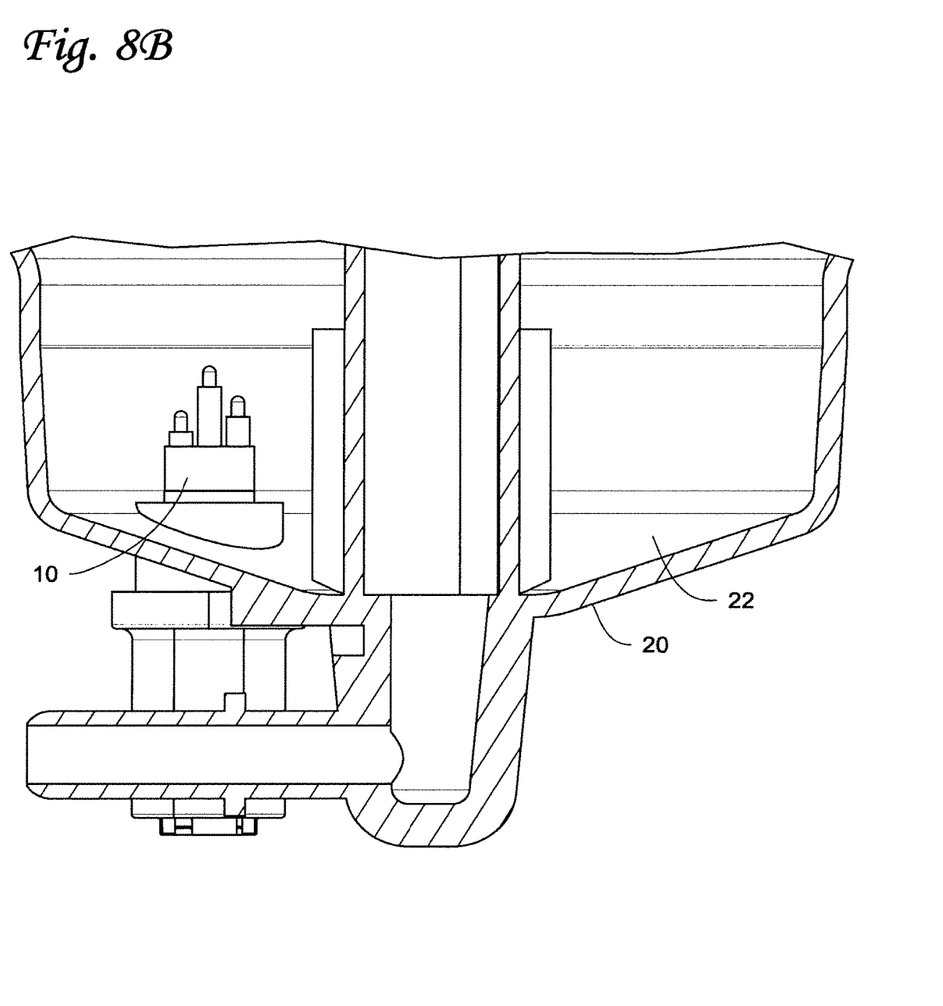
FIG. 8B shows an embodiment of a water in fuel sensor vertically installed in a water sump of a fuel filter/fuel water separation housing.

FIG. 8A shows another embodiment of a water sensor 800. The water sensor 800 is shown configured with single cylindrical rod with a stack or series of conductors (contacts) 802a, 802b, 802c and insulators 810 to allow for water detection at multiple levels. Distinguishing between the various water levels could be accomplished as discussed above, by communicating to the ECU with a wire for each contact on the water sensor, and/or by integrating resistors between pairs of contacts as described in earlier embodiments, such that the ECU "reads" the resistance value across the two sensor wires and interprets the resistance value as a specific water level. FIG. 8B shows vertical installation of a water in fuel sensor, e.g. sensor 10, in a housing 20 of a filtration apparatus with a sump or collection area 22.

Figure 9:
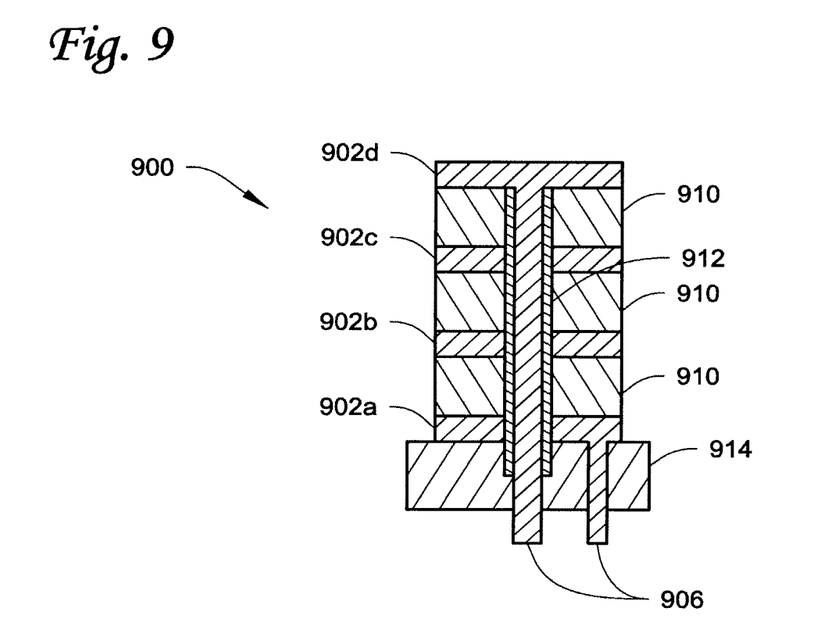
FIG. 9 shows a schematic of an embodiment of a multiconductor water in fuel sensor that is vertically stacked, showing spacers between contacts.

With reference to FIG. 9, another embodiment of a water sensor 900 is shown with another embodiment of insulators that may be employed. The water sensor 900 has a main body 914 with electrical connectors 906. As shown, the insulators could be replaced with resistive material as spacers 910 between contacts 902a, 902b, and 902c, 902d. The resistive material may be a material such as that used in surface mount resistors.

As an alternative, the spacers 910 may be constructed as a coil type resistor formed in the space between contacts 902a, 902b, 902c, 902d, and are encapsulated by an insulating material such as ceramic or plastic. In this way, the spacers physically separate the contacts, and also serve as the resistors. If appropriate an insulating sleeve 912 may be employed to insulate the sensor contacts. The ECU would read the resistance between the top and bottom conductors in the stack to determine the water level. As shown in FIG. 9, four contacts are shown, but it will be appreciated that any number ≥3 contacts will work. In some instances, more contact/resistor groups may provide more distinct water levels that can be detected. A two contact/resistor stack may detect only a single water level, and water level increase rate could not be calculated, though this too could be useful in some applications.

Figure 10:
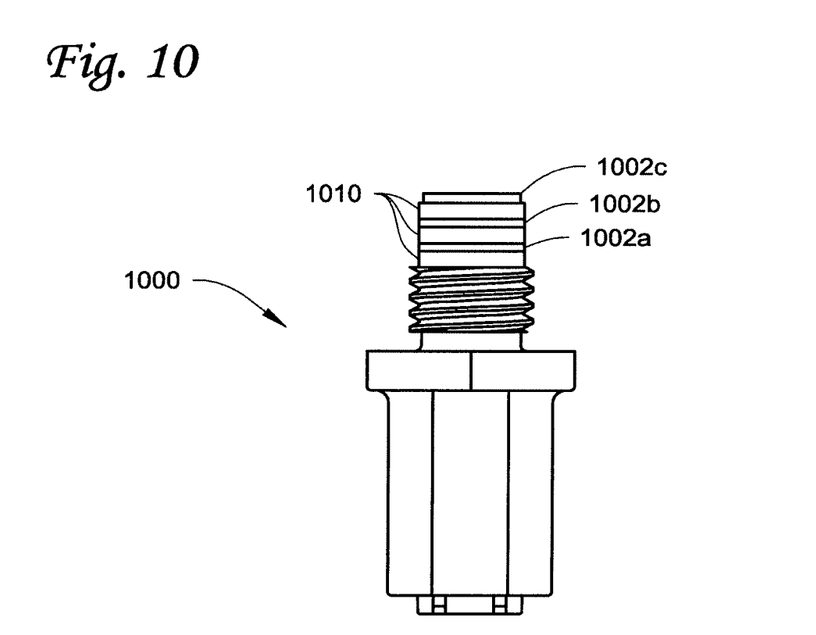
FIG. 10 shows another embodiment of a multiconductor water in fuel sensor that is vertically stacked.
Figure 11A:
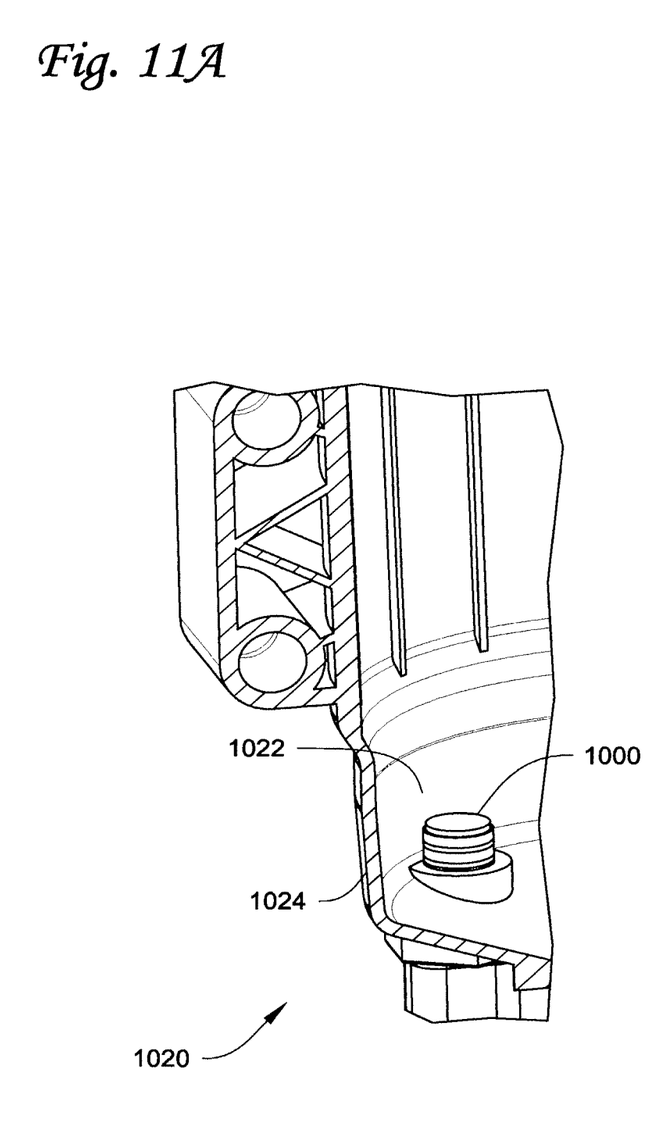
FIG. 11A shows an embodiment of a vertical installation of the multiconductor water in fuel sensor of FIG. 10 showing the multiconductor water in fuel sensor installed in a water sump of a fuel filter/fuel water separation housing
Figure 11B:
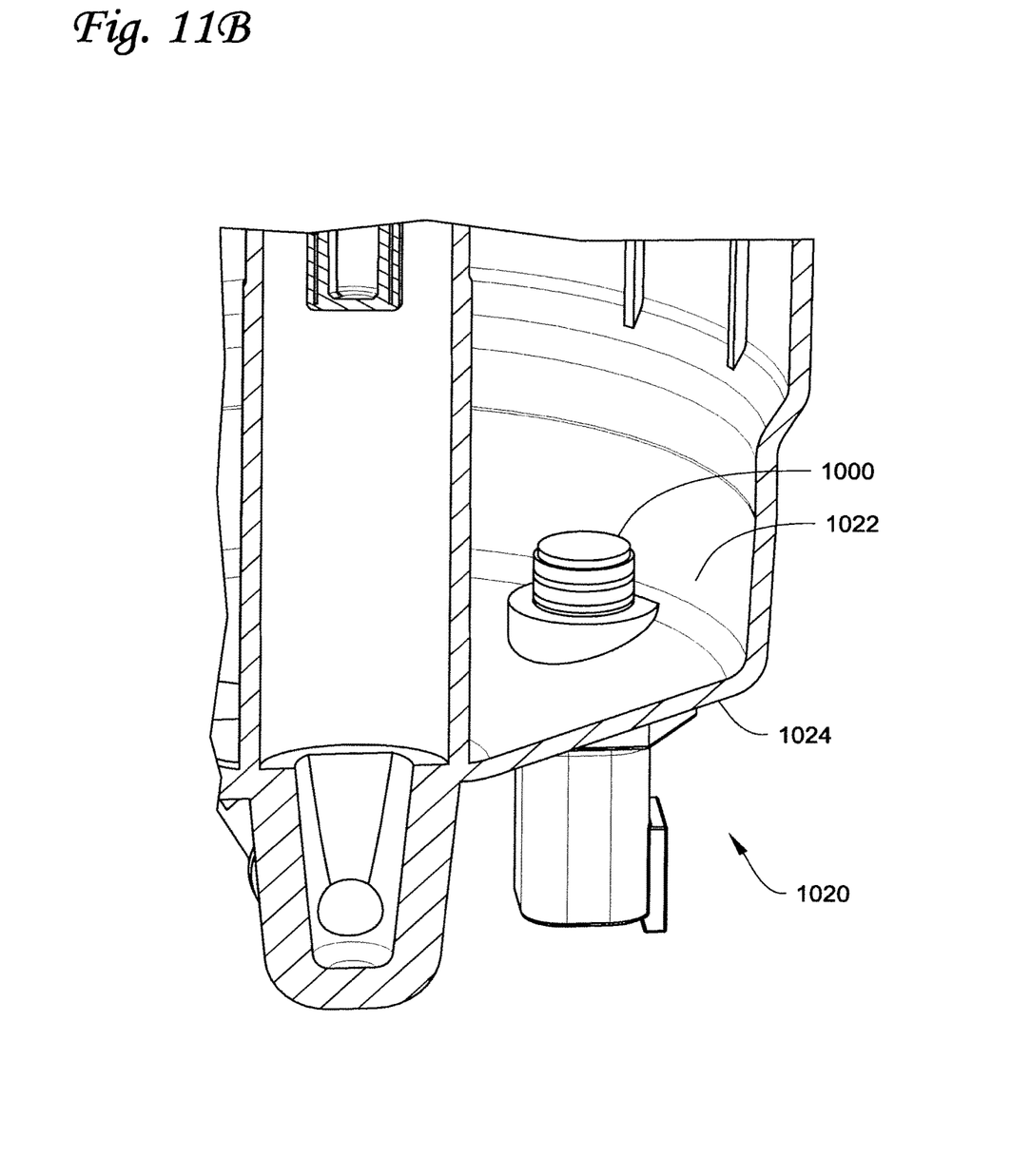
FIG. 11B shows another view of a vertical installation of the multiconductor water in fuel sensor of FIG. 10.

FIGS. 10 and 11A-B show a water sensor 1000 with an alternative embodiment of stacked resistance rings.

FIGS. 10 and 11A-B show the water sensor 1000 to have three same size stainless steel rings (conductor) 1002a, 1002b, 1002c with resistance embedded in plastic body. It will be appreciated the more than three rings may be employed. As shown, these rings 1002a, 1002b, 1002c are separated with insulator materials 1010. Each conductor can be configured to have a different resistance value, which signifies a different zone. For example, the resistance value of each ring 1002a, 1002b, 1002c signifies a different zone, which can be indicated for example by color, e.g. green for contact 1002a, yellow for contact 1002b, and red for contact 1002c.

These zones are defined to calculate time of water rising, for example in a sump 1022 within a housing 1024 of a fuel filtration apparatus 1020. The rising level of water into the sump 1022 will kick off timer in the ECU as soon as it touches the green zone. As soon as water touches the red zone, the ECU will calculate time duration and if it is less than pre-determined time then it will alert an operator, for example on a vehicle dashboard where a vehicle operator can see it.

FIG. 10 shows an embodiment of the water sensor 1000 described above. FIGS. 11A-B show the water sensor 1000 vertically installed in the water sump 1022 of a fuel filter 1020/FWS housing 1024.

Typical water sensors have only one position of detection. In other words, they indicate when the water reservoir is "full" but do not measure a rate at which the reservoir is filling. So an operator, for example a vehicle operator, has no idea if the reservoir is filling slowly over a long period (normal) or they received a bad batch of fuel, containing a high volume of water (abnormal). The latter case can ultimately lead to biological growth, corrosion, deposition, and filter plugging. In contrast, the water sensors herein allow the vehicle operator to be notified in case of high water content, so corrective action may be taken. The following provides some structural and functional benefit in the improved water sensor designs described herein.

1) Satisfies a means to detect when a large concentration of water has entered the tank, so the driver may be notified before damage is caused.

2) Provides a water sensor with three or more sensor contacts allowing detection of two or more different water levels.

3) The water sensor allows an engine control unit (ECU) to track time when each water level is reached to determine if rate of water filling meets an alarm value.

The invention may be embodied in other forms without departing from the spirit or novel characteristics thereof. The embodiments disclosed in this application are to be considered in all respects as illustrative and not limitative. The scope of the invention is indicated by the appended claims rather than by the foregoing description; and all changes which come within the meaning and range of equivalency of the claims are intended to be embraced therein.

What is claimed is:

1. A method of determining whether fuel has high water content, comprising:
   providing a water-in-fuel sensor in a fuel filtration apparatus, the water-in-fuel sensor comprising a main body having a first end and a second end, at least one electrical contact disposed proximate the first end, the at least one electrical contact operatively connectable to an electronic control unit; and multiple sensor contacts disposed proximate the second end, each of the multiple sensor contacts configured to detect water at different water levels and provide an output depending on whether water is detected at each of the respective multiple sensor contacts;
   measuring the resistance across the multiple sensor contacts during two time points;
   comparing a time interval between the two time points to a pre-defined time interval; and
   in response to the time interval being less than the pre-defined time interval, determining that the fuel has high water content.

2. The method of claim 1, further comprising, in response to determining that the fuel has high water content, triggering an alarm.

3. The method of claim 2, wherein the alarm comprises a visual indicator.

4. The method of claim 2, wherein the alarm comprises an audio indicator.

5. The method of claim 1, wherein each of the multiple sensor contacts are resistance sensors, and wherein a resistance across the multiple sensor contacts is dependent on the water level.

6. The method of claim 1, wherein the electronic control unit is configured to detect a rate of change of water accumulation by measuring the resistance across the multiple sensor contacts during at least two time points.

7. The method of claim 1, wherein the water-in-fuel sensor is a part of a filtration module, wherein the filtration module comprises a collection compartment.

8. The method of claim 7, wherein the water-in-fuel sensor is positioned within the collection compartment and the collection compartment is configured to collect water filtered from fuel.

9. The method of claim 1, wherein the filtration module is a part of a filtration system, wherein the filtration system comprises the electronic control unit and a fuel filter.

10. The method of claim 1, wherein the at least one electrical contact is configured to send the output from each of the multiple sensor contacts to the electronic control unit.

11. The method of claim 1, wherein each of the multiple sensor contacts are configured to contact water at the different water levels.

12. The method of claim 1, wherein the multiple sensor contacts comprise pins extending from the main body, the pins having different lengths from each other.

13. The method of claim 1, wherein the multiple sensor contacts extend from the main body, the multiple sensor contacts each having substantially the same length.

14. The method of claim 1, wherein the water-in-fuel sensor further comprises a threaded connective portion on the main body, the threaded connective portion is clocked so as to obtain a relative arrangement of the multiple sensor contacts so that the multiple sensor contacts are aligned with each other along a vertical axis when the water-in-fuel sensor is installed into a filter module, and wherein the multiple sensor contacts are configured as pins that extend horizontally from the main body when the water-in-fuel sensor is installed.

15. The method of claim 1, wherein the multiple sensor contacts are configured as rings.

16. The method of claim 1, wherein the multiple sensor contacts are disposed on a single rod, such that the multiple sensor contacts are configured in a stack with one of insulators or spacers between the multiple sensor contacts.

17. The method of claim 1, wherein a first time point of the two time points comprises a time at which the water level corresponds to a first sensor contact of the multiple sensor contacts, and wherein a second time point of the two time points comprises a time at which the water level corresponds to a second sensor contacts of the multiple sensor contacts.

18. A method of determining whether fuel has high water content, comprising:
  providing a water-in-fuel sensor in a fuel filtration apparatus, the water-in-fuel sensor comprising multiple sensor contacts, each of the multiple sensor contacts configured to detect water at different water levels and provide an output depending on whether water is detected at each of the respective multiple sensor contacts;
  measuring the resistance across the multiple sensor contacts during two time points;
  comparing a time interval between the two time points to a pre-defined time interval; and
  in response to the time interval being less than the pre-defined time interval, determining that the fuel has high water content.

19. The method of claim 18, further comprising, in response to determining that the fuel has high water content, triggering an alarm comprising a visual indicator.

20. The method of claim 18, further comprising, in response to determining that the fuel has high water content, triggering an alarm comprising an audible indicator.

* * * * *